United States Patent [19]

Thorne et al.

[11] 3,983,164

[45] Sept. 28, 1976

[54] PHENYL ALKYLENEOXY PHENYL ALKANOIC ACID ESTERS

[75] Inventors: David Edward Thorne, Cranleigh; Keith Howard Baggaley, Redhill; Brian Morgan, Reigate, all of England

[73] Assignee: Beecham Group Limited, Great Britain

[22] Filed: Aug. 5, 1974

[21] Appl. No.: 495,119

[30] Foreign Application Priority Data
Aug. 23, 1973 United Kingdom............ 39902/73
Sept. 11, 1973 United Kingdom............ 42654/73
Mar. 26, 1974 United Kingdom............ 13911/74

[52] U.S. Cl. .................. 260/473 R; 260/521 R; 260/516; 260/569; 260/470; 260/559.S; 260/559 T; 424/308; 424/317; 424/324

[51] Int. Cl.² ............... C07C 69/88; C07C 69/78

[58] Field of Search........... 260/473 R, 521 R, 516, 260/569, 470, 559 S, 559 T; 424/308, 324, 317

[56] References Cited
UNITED STATES PATENTS
3,166,531   1/1965   Horn.................................. 260/49

OTHER PUBLICATIONS
Bost et al., J. Am. Chem. Soc., vol. 74, (1952), pp. 1821–1824.
Chem. Abst., 8th Collective Index (1967–1971), pp. 4159S–4160S.

*Primary Examiner*—Lewis Gotts
*Assistant Examiner*—D. R. Phillips

[57] ABSTRACT

Pharmaceutical compositions having hypolipidaemic and/or hypoglycaemic activity, contain a substituted (4-carboxyphenoxy) phenyl alkane derivative.

22 Claims, No Drawings

PHENYL ALKYLENEOXY PHENYL ALKANOIC ACID ESTERS

This invention relates to compounds which have hypolipidaemic activity, to a method for their preparation and to pharmaceutical compositions comprising them. Many of the compounds of this invention in addition have a degree of hypoglycaemic activity.

It is often found that patients with occlusive vascular disease may be pre-diabetic so it would be advantageous of a drug administered to reduce serum lipid levels should act prophylactically to prevent the hypoglycaemic state. Furthermore in conditions such as diabetes mellitus, many sufferers also suffer from elevated from levels of lipid (for example cholesterol, phospholipid and/or triglyceride) in the blood. It is therefore advantageous that a hypoglycaemic drug which reduces blood sugar levels should also possess lipid lowering activity.

It has been disclosed that certain substituted benzoic acids have the ability to lower serum lipids when administered to mammals although such compounds are not known to effect the level of sugar in the blood. The activity of these benzoic acids was demonstrated in U.S. Pat. No. 3,716,644 where details may be found of the preparation and activity of compounds of, inter alia, formula (I):

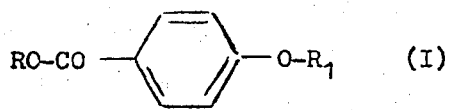

where R is hydrogen, lower alkyl, phenyl, benzyl, 3-pyridyl and 2-dimethylaminoethyl and $R_1$ is a $C_{12-20}$ alkyl group.

We have now found a class of substituted ethers which have useful pharmacological properties, individual compounds within this class having useful hypolipidaemic and also hypoglycaemic activity. It is clear therefore that this class of substituted ethers have considerable advantages over the compounds disclosed in U.S. Pat. No. 3,716,644.

Accordingly the present invention provides a pharmaceutical composition which comprises one or more pharmaceutically acceptable carriers together with a compound of formula (II):

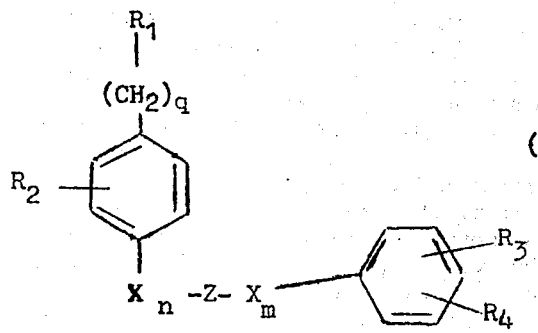

wherein X is a straight chained or branched chained alkylene group of 1 to 6 carbon atoms; $R_1$ is a carboxylic acid group or a group capable of being converted in the human body to a carboxylic acid group; $R_2$ is a hydrogen atom or a lower alkoxyl group; $R_3$ is a hydrogen or halogen atom or a lower alkyl, lower alkoxyl, halo lower alkyl or nitro group $R_4$ is a hydrogen or halogen atom or a lower alkyl, lower alkoxyl, halo lower alkyl or nitro group; 1 is zero or one; and one of m and n is zero and the other is one. When used herein, the adjective "lower" means that the group to which it applies contains from 1 to 6 carbon atoms.

Suitable lower alkyl groups for $R_3$ and $R_4$ include the methyl, ethyl and straight and branched chained propyl and butyl groups.

Preferred lower alkoxy groups for $R_2$, $R_3$, or $R_4$ include methoxy and ethoxy groups.

A preferred halo lower alkyl group for $R_4$ is the trifluoromethyl group.

Suitable examples of lower-alkylene groups for X include methylene, ethylene, and propylene, preferably methylene. The lower-alkylene-oxy group may be for example methyleneoxy, ethyleneoxy, n- and sec-propyleneoxy, n-, sec-, iso-, or tert-butyleneoxy, -pentylenoxy and hexyleneoxy. A preferred such group is the n-hexyleneoxy group. A preferred alkylenethio group is ethylenethio.

Suitable groups capable of conversion in the body to carboxyl groups include for example salts, esters, amides and hydrazides of the carboxyl group; alkyl groups wherein: $R_1$ is a carboxylic acid group or a group capable of being converted in the human body to a carboxylic acid group;

$R_2$ is a hydrogen atom, a lower alkyl group or a lower alkoxyl group;

$R_3$ is a hydrogen or halogen atom, or a lower alkyl or lower alkoxyl group;

$R_4$ is a hydrogen or halogen atom, or a phenyl, lower alkyl, lower alkoxyl, halo-lower alkyl, nitro or carboxylic ester group; or $R_3$ and $R_4$ together form the residue of a benzene ring;

Z is oxygen or sulphur;

X is a straight or branched lower alkylene, lower-alkylene-oxy, lower-alkylene-thio, or lower-alkylene-carbonyl group;

q is zero or an integar from 1–12; and one of m and n is zero and the other is one.

One sub-group of compounds which may advantageously be incorporated into the compositions comprises compounds of formula (III):

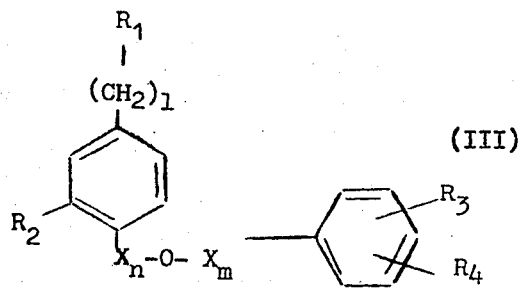

(especially straight chained alkyl groups containing an odd number of carbon atoms); alkyl groups substituted by one or more hydroxyl groups; nitrile, aldehyde, acyl groups and carboxyl-substituted acyl.

Suitable esters include alkyl esters, preferably lower-alkyl esters.

One especially useful group of compounds for use in the compositions of this invention is represented by formula (IV):

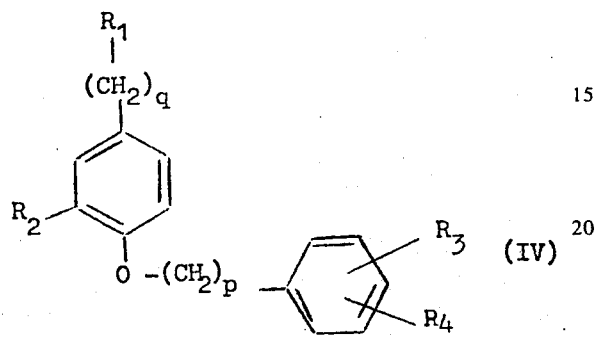

wherein $R_1$, $R_2$, $R_3$, $R_4$ and q are as defined in relation to formula (II), and p is 1, 2 or 3.

For a compound to have maximum potential as a hypolipidaemic agent, it must significantly decrease serum lipid levels and have little or no effect on growth, liver weight and liver lipid. Within compounds of formula (IV) such a combination of parameters are best satisfied wherein p is 1 and $R_2$ is hydrogen especially when either $R_1$ is a carboxyl group or a salt, ester, amide or hydrazide thereof when q is 0 or $R_1$ is methyl, hydroxymethyl or a carboxyl group or a salt, ester, amide or hydrazide thereof when q is an integer from 1 to 12.

Preferred compounds of formula IV for hypolipidaemic activity include those wherein $R_3$ is hydrogen and $R_4$ is hydrogen, lower alkyl, especially methyl, halogen, especially fluorine or bromine, or lower alkoxy. For example, specific compounds of formula (IV) which have preferred properties are:

4-ethoxycarbonylphenoxyphenyl methane;
4-ethoxycarbonylphenoxy - (4'fluorophenyl) methane;
4-ethoxycarbonylphenoxy - (4'-bromophenyl) methane;
4-ethoxycarbonylphenoxy - (4'methylphenyl) methane;
4-carboxyphenoxyphenyl methane;
4-(ethoxycarbonylmethyl) phenoxy-(2'-methoxyphenyl) methane.

As indicated above, individual compounds or subclasses of compounds of this invention have different specific hypolipidaemic and/or hypoglycaemic activity. We have noted preferred compounds having hypoglycaemic activity in addition to hypolipidaemic activity are those of formula (IV) wherein $R_1$ is an alkyl or a carboxylic acid or ester group, p is 1, $R_2$ is H, $R_3$ is H and $R_4$ is selected from hydrogen, 4-chloro, 4-methyl. Specifically, preferred hypoglycaemic compounds are:

4-ethoxycarbonylphenoxyphenylmethane;
4-ethoxycarbonylphenoxy-(4'-chlorophenyl)-methane;
4-ethoxycarbonylphenoxy-(4'-methylphenyl)-methane;
4-methylphenoxyphenylmethane.

Another group of compounds having good hypolipidaemic activity and useful in the compositions of this invention is represented by formula (V):

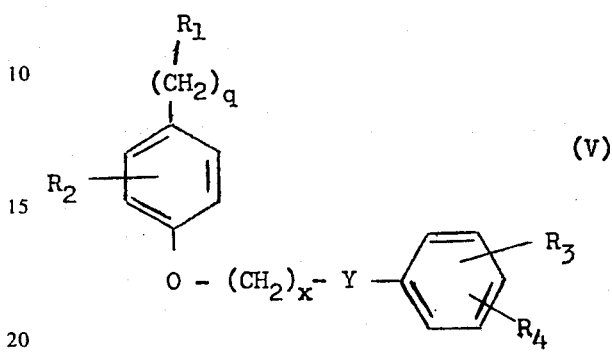

wherein $R_1$, $R_2$, $R_3$, $R_4$ and q are as defined above with respect to formula (II), x is an integer from 1 to 6 and Y is oxygen or sulphur.

Preferred compounds of formula (V) include those wherein q is 0, $R_1$ is a carboxyl group or a salt, ester amide or hydrazide thereof, $R_2$ is hydrogen, and Y is oxygen. Preferably within this class, the integer x is 6. For example a preferred compound within the group of formula V is:

n-1-[4-ethoxycarbonylphenoxy]-6-[4'-chlorophenoxy] hexane.

A further useful group of compounds for the present compositions is represented by formula (VI):

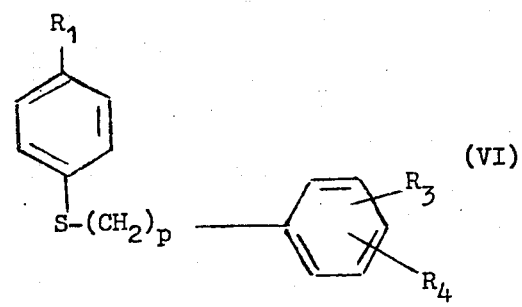

wherein $R_1$, $R_3$ and $R_4$ are as defined with respect to formula (II) above and p is 1, 2 and 3.

An example of a preferred compound within this class is 4-methylphenylthio-(4'-methylphenyl) methane.

As in common practice, the compositions of the invention will usually be accompanied by or associated with written or printed directions for use in the medical treatment concerned, in this case, as an agent for controlling or reducing serum lipid levels and/or serum sugar levels or for use in prevention or treatment of atherosclerosis, or diabetes.

In forming the novel compositions of this invention the compound is incorporated in a suitable carrier such as for example, a pharmaceutical carrier, beverage or foodstuff. The compositions may take the form of tablets, linguets, powders, capsules, slurries, troches or lozenges. Any suitable pharmaceutical carrier may be used for formulating solid compositions such as, for example, magnesium stearate, starch, lactose, glucose, sucrose, rice flour, talc and chalk. The composition may also be in the form of an ingestible capsule (e.g. of gelatin) to contain the compound; or in the form of a syrup, a liquid solution or a suspension.

Suitable liquid pharmaceutical carriers include ethyl alcohol glycerine, saline and water together with flavouring or colouring agents to form syrups. Also, the compound may be incorporated in a foodstuff such as, for example, in combination with biscuits.

Preferred dosage forms include unit dosage forms such as tablets, capsules and the like.

The majority of the compounds of formula (II) are novel compounds. Thus in a further aspect, this invention provides novel compounds of formula (II) above wherein $R_1$, $R_2$, $R_3$, $R_4$, X, Z, $q$, $m$, and $n$ are as previously defined in relation to formula (II), provided that: when $n$ and $q$ are zero, Z is oxygen, X is $CH_2$, $R_1$ is $CO_2H$ or an ester thereof and $R_3$ is hydrogen, then $R_4$ is not hydrogen, 2-, or 3- methyl, chloro or nitro.

Thus, particularly useful sub-groups of novel compounds include, inter alia, those of formula (VII), (V), (VIII), (IX) shown below:

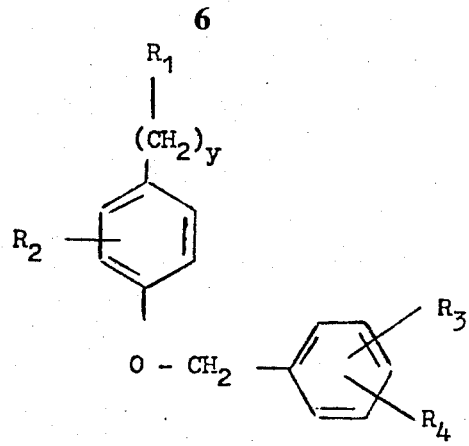

wherein $R_1$, $R_2$, $R_3$, and $R_4$ are as defined above with respect to formula (II) and $y$ is an integer from 1 to 12;

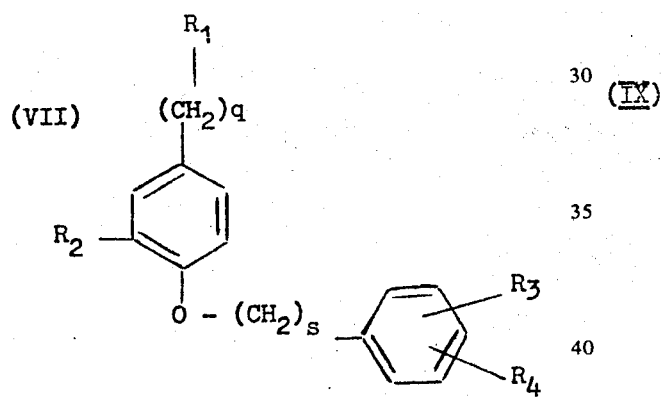

wherein $R_1$, $R_2$, $R_3$, $R_4$ and $q$ are as defined with respect to formula (II) and $s$ is an integer from 2 to 6;

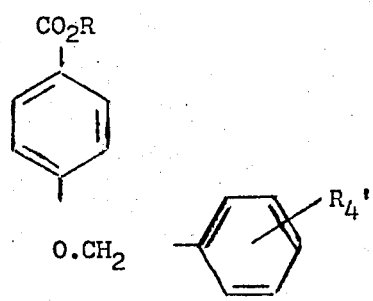

wherein R is hydrogen or a lower alkyl group, and $R_4'$ is a fluorine, bromine or iodine atom, or a 4-methyl group.

Preferred compounds of formula (V) are those stated above as preferred for use in the compositions of the invention.

Preferred compounds of formula (VIII) include those wherein $R_2$ is hydrogen and $R_1$ is methyl, hydroxymethyl, or a carboxyl group or a salt, ester, amide or hydrazide thereof. Within this class, preferably $R_3$ is hydrogen and $R_4$ is lower alkoxy. For example a preferred compound within the formula (VIII) is: 4-(ethoxycarbonylmethyl) phenoxy -(2'-methoxyphenyl) methane.

Preferred compounds having formula (IX) include:
4-ethoxycarbonylphenoxy - (4'-fluorophenyl) methane;
4-ethoxycarbonylphenoxy - (4'-bromophenyl) methane;
4-ethoxycarbonylphenoxy - (4'-methylphenyl) methane.

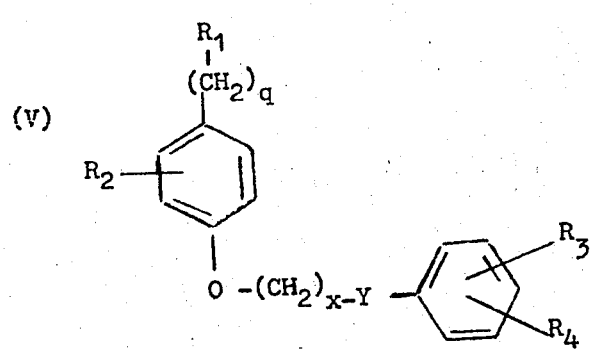

wherein $R_1$, $R_2$, $R_3$, $R_4$ and $q$ are as defined with respect to formula (II), $x$ is an integer from 1 to 6 and Y is oxygen or sulphur;

The novel compounds of the present invention may be prepared by the reaction of a compound of the formula

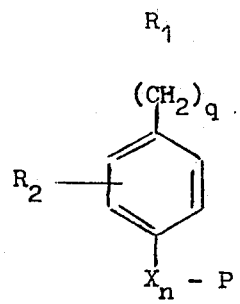

(X)

with a compound of formula XI

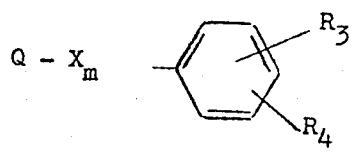

(XI)

wherein $p$ is -ZH (where Z is defined with reference to formula (II) ) or a reactive derivative thereof, when $n$ is 0 or is a readily displaceable group when $n$ is 1; and Q is -ZH or a reactive derivative thereof when $m$ is 0 or is a readily displaceable group when $m$ is 1, and wherein $R_1$, $R_2$, $R_3$, $R_4$, X, $q$, $n$, and $m$ are as defined with reference to formula (II) above provided that when $n$ and $q$ are zero, Z is oxygen and X is $CH_2$, $R_1$ is $CO_2H$ or an ester thereof and $R_3$ is hydrogen, then $R_4$ is not hydrogen, chloro nitro, or 2- or 3- methyl, and optionally thereafter converting at least one group $R_1$, $R_2$, $R_3$ and $R_4$ to a different such group.

Reactive derivatives of the group -ZH include salts and other derivatives which increase the nucleophilicity of the atom Z.

By a "readily displaceable group" is meant an atom or group displaceable by a nucleophilic centre (such as the lone pair electrons on a hydroxyl oxygen or alkoxide ion). Such groups include halides such as I, Br or Cl; pseudo-halides such as the azido group $N_2$-; active esters such as the groups -$O.SO_2CH_3$, $O.SO_2C_6H_4CH_3$, $O.CO.OC_2H_5$; compounds prepared in situ from dehydrating agents such as carbodiimides or carbonyldiimidazoles, phosphorus pentachloride, phosphoryl chloride, thionyl chloride, or phosphorus pentoxide; or other such good leaving groups.

For the preparation of compounds wherein Z is oxygen the group -ZH is a hydroxyl group. If the hydroxyl compound used in the above condensation reaction is in the form of a salt, it is generally in the form of the sodium or potassium salt.

When the condensation reaction uses a salt as one of the reactants, the salt is preferably produced by means of a strong base, for example, sodium hydride, sodamide, or a sodium alkoxide or sodium methoxide. Suitable solvents for the reaction include dimethylformamide or dimethylsulphoxide (especially when employing sodium hydride or sodamide as base), methanol (when using sodium methoxide) and ethanol (when using sodium ethoxide).

Alternatively the free hydroxyl group in compound (X) or (XI) may be employed and the process is then carried out in the presence of the acid acceptor, for example a tertiary organic base such as pyridine, triethylamine or N-methylpyrrolidine; or potassium carbonate (in acetone as solvent).

Another example of a readily displaceable group on the intermediate (XI) when Z = oxygen is the residue of a dimethylformamide acetal the intermediate having formula (XII):

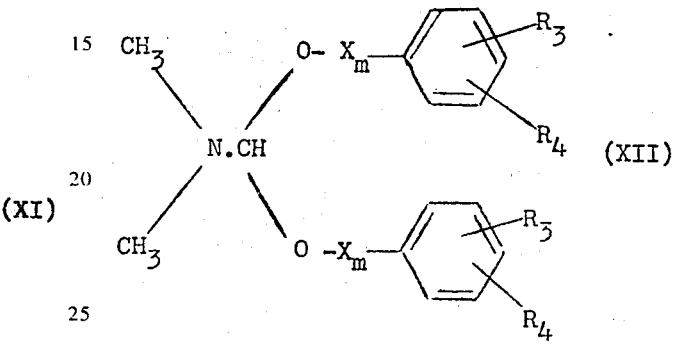

For the preparation of compounds of formula (II) wherein Z is sulphur the group -ZH is a thiol group. Such a group may be used in the above condensation either as the free thiol or as a salt thereof. Alternatively, for the preparation of the Z=S compounds of formula (II) wherein $q$ is zero, and $n$ is zero, a reactive derivative which may be used as a dimer of formula (XIII):

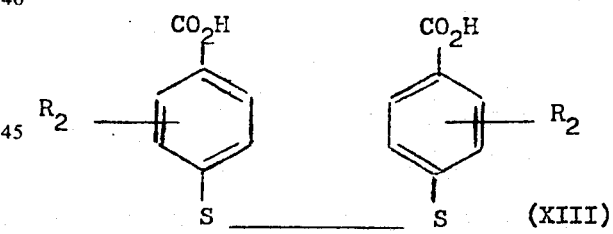

as an intermediate (X)

It may be preferable to modify the substituents $R_1$, $R_2$, $R_3$ and/or $R_4$ after the condensation reaction rather than before. Thus, it is preferable, when preparing compounds of formula (II) wherein $R_1$ includes an amide or carboxylic acid group, first to prepare the corresponding compound with a carboxylic acid ester group and then to convert such group to carboxylic acid group or amide by conventional means. It may be noted that some of the compounds wherein $R_1$ is an alkyl ester are difficult to hydrolyse to the corresponding carboxylic acid group and it is often convenient to prepare the benzyl ester by the above condensation, which ester is more readily hydrolysed.

Similarly, if the group R₁ contains a hydroxyl group, it may be advantageous to first protect it by forming a readily hydrolysable ester which can be removed subsequent to the condensation reaction.

Alternative methods of preparing compounds wherein R₁ contains an ester group include the esterification of the free acid or its salt or other reactive derivative of the acid, or transesterification of a compound having a different ester group. Esterification may be performed by any conventional method, for example by reaction of the free acid: (a) with the appropriate alcohol in the presence of a catalyst such as a strong acid, dry hydrogen chloride, or p-toluenesulphonic acid, or (b) with the appropriate halide or sulphate of the alcohol in the presence of dimethylsulphoxide and calcium carbonate or with the halide in the presence of hexamethylphosphoramide or (c) by phase transfer catalysis methods with the halide and/or sulphate of the alcohol in aqueous and/or organic solution in the presence of a quaternary ammonium salt such as tetrabutyl ammonium bisulphate or halide, or benzyltrimethylammonium halide.

The formation of compounds (II) wherein R₁ is an ester may also be carried out by conventional transesterification methods, for example reaction of an ester with the appropriate second alcohol in the presence of a catalyst such as the sodium salt of the alcohol, or dry hydrogen chloride, p-toluenesulphonic acid, or potassium cyanide.

Compounds of formula (II) wherein R₁ is an ester may also be prepared by alkanolysis of the corresponding nitrile (R₁—C≡N); or by hydrolysis of an iminoether compound having formula (II) wherein R₁ is a group of formula:

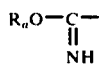

wherein $R_a$ is the hydrocarbon residue of an alcohol or phenol.

Compounds wherein R₁ contains a carboxyl group may be prepared by oxidation of the corresponding precursor having formula (II) wherein R₁ is selected from:
a. formyl;
b. methyl;
c. hydroxymethyl;
d. vinyl, or substituted vinyl;
e. acyl Examples of the reagents which may be employed to effect such oxidations include respectively,
a. basic silver oxide, or concentrated nitric acid;
b. acidic sodium or potassium dichromate;
c. manganese dioxide followed by basic silver oxide;
d. aqueous potassium permanganate in an organic solvent such as benzene in the presence of a quaternary ammonium salt such as a tetrabutylammonium halide;
e. a hypohalite. The acyl group may be an acetyl group (CH₃CO). Preferably the hypohalite reactant is sodium hypohalite which may be generated in situ in aqueous solution by the reaction of sodiumhydroxide on a mixture of iodine and potassium iodide.

The desired free acid may be isolated and converted to any desired salt by known methods.

Compounds wherein R₁ contains a carboxylic acid group can also be prepared by the acid or base catalysed hydrolysis of the corresponding compound of formula (II) wherein R₁ is selected from:
a. carboxylic acid amide group;
b. nitrile group (-C≡N);
c. esterified carboxylic acid group Hydrolysis of amides may be carried out using a mineral acid as catalyst, suitably hydrochloric acid or sulphuric acid. Base catalysed hydrolysis may be carried out using an alkali metal or alkaline earth metal hydroxide, e.g. sodium or potassium hydroxide. Suitably the hydrolysis reaction is carried out in aqueous solution and fairly severe reaction conditions are preferred, e.g. refluxing for several hours. The desired compound can be isolated as the free acid by neutralisation of the resultant reaction mixture or as the appropriate base addition salt (e.g. sodium salt if sodium hydroxide was employed) or acid addition salt (e.g. the hydrochloride if HCl was employed). Alternatively the free acid can be converted to any desired salt by standard procedures.

For the hydrolysis of a compound wherein R₁ is a nitrile group, ammonia is liberated and thus the preferred catalyst is an acid which will bind the ammonia e.g. a hydrogen halide such as HCl or HBr. If base catalysed hydrolysis is used, ammonia is liberated and the acid will be obtained as an alkali salt or, after neutralization, as the free acid.

For the hydrolysis of an esterified carboxylic acid group, preferably the process involves hydrolysis with a strong base such as sodium hydroxide. The esterified carboxylic acid groups R₁ may be, for example lower alkoxycarbonyl groups such as methoxycarbonyl or tertiary butoxycarbonyl groups. The remarks made earlier about salts of the resultant free acid also apply in this case.

A further method for the preparation of compounds of formula (II) wherein R₁ is a carboxylic acid group comprises the carbonation of a compound of formula (II) wherein R₁ is a group of formula:

—MX followed by hydrolysis, wherein M is magnesium, calcium or lithium and X is chlorine, bromine or iodine. Such reagents are of course well known in the art and may be prepared by known methods. Carbonation is preferably carried out using aqueous carbondioxide but solid carbon dioxide may be used on occasions. Hydrolysis of the intermediate formed after carbonation can be carried out simply by the addition of water.

Compounds of formula (II) wherein R₁ is a hydroxymethyl group ma be prepared by reduction of the compound wherein R₁ is a formyl or ester group.

The above processes also form an aspect of this invention as do the useful novel intermediates of the formula (XIV):

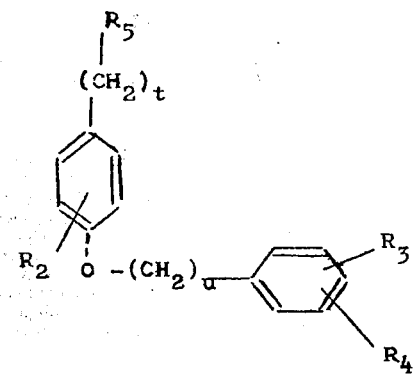

where $R_5$ is a CN or CHO group, $t$ is zero or an integer from 1 to 12, $u$ is an integer from 1 to 6 and $R_2$, $R_3$ and $R_4$ are as defined in relation to formula (II).

Preferred compounds of formula (XIV) include those where $u$ is 1 and $t$ is zero.

Also included within the scope of the present invention is a method for controlling or reducing the serum lipid levels of animals, including man which method comprises the administration to the animal or man of one or more of the compounds of formula (II) above. An oral administration is preferred.

The compound may be administered alone in combination with one or more pharmaceutically acceptable carriers, or as part of the total dietary intake. In the latter case, the amount of said compound employed may be less than 1% by weight of the diet and is preferably no more than 0.5% by weight. The diet for a man may consist of normal foodstuffs to which the ester has been added, and similarly the diet for animals may consist of foodstuffs and the compound may be added alone or with a premix.

In order to achieve an effective degree of serum-lipid lowering, the compound shoul preferably be administered to the animal or patient in an amount of from 1 to 10 g. per day; generally it will be most convenient to spread the daily dosage by giving several smaller, more palatable doses.

The following Examples illustrate the present invention:

EXAMPLE 1

GENERAL METHODS OF PREPARATION

Example 1A

Condensation Using an Alkoxide as base
(4-Ethoxycarbonylphenoxy-4-chlorophenyl methane)

To a solution of ethyl 4-hydroxybenzoate (8.3g) in sodium ethoxide solution (1.15g. sodium in 70 ml. of absolute ethanol) was added p-chlorobenzylchloride (8.1g.) in one portion. The mixture was heated under reflux for 16 hours, allowed to cool and poured into water (500 mls.) and the product extracted into ether. The organic layer was separated and dried (anhydrous $MgSO_4$) and filtered. Evaporation of the solvent under reduced pressure gave the crude product which on recrystallization from methanol, yielded by 4-ethoxycarbonylphenoxy-4-chlorophenyl methane (8.5g.), m.pt. 83°–84°C.

EXAMPLE 1B

Condensation Using Sodium Hydride as base
(4-Ethoxycarbonylphenoxyphenyl methane)

Sodium hydride (4.8g. of 50% suspension in oil) was added to a solution of ethyl p-hydroxybenzoate (166g.) in dimethylformamide (1 l). Benzyl chloride (126 g.) was added dropwise to the solution and the mixture heated on a steam bath for 2 hours. The solution was allowing to cool and ethanol (100 mls.) was added and the mixture poured into water (3 l) and then extracted with chloroform. The organic layer was dried (anhydrous $MgSO_4$), filtered and the solvent removed under high vaccum. The resulting crude product was recrystallized from ethanol to yield pure 4-ethoxycarbonylphenoxyphenyl methane (154.2g.), b.pt. 172–3 at 10mm Hg.

EXAMPLES 2–26

The following compounds have been prepared by the general methods of Examples 1A and/or 1B. All compounds had spectral characteristics and chemical analyses consistent with the assigned structures. The compounds thus produced are of formula:

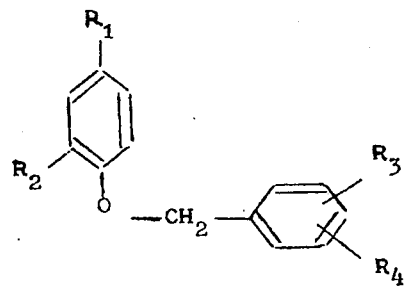

| Example No. | Compound | $R_1$ | $R_2$ | $R_3,R_4$ | M.P. (°C) | B.P. (°C/MM) |
|---|---|---|---|---|---|---|
| 2 | 4-Ethoxycarbonylphenoxyphenyl-methane | $CO_2Et$ | H | H,H | | 172°/10 |
| 3 | 4-Ethoxycarbonylphenoxy-3'-chlorophenyl methane | $CO_2Et$ | H | H,3-Cl | 54–55° | |
| 4 | 4-Ethoxycarbonylphenoxy-2',5'-dichlorophenyl methane | $CO_2Et$ | H | 2,5-di-Cl | 62–63° | |
| 5 | 4-Ethoxycarbonylphenoxy-3',4'-dichlorophenyl methane | $CO_2Et$ | H | 3,4-di-Cl | 99° | |
| 6 | 4-Ethoxycarbonylphenoxy-4'-fluorophenyl methane | $CO_2Et$ | H | H,4-F | 60–2° | |
| 7 | 4-Ethoxycarbonylphenoxy-3'-trifluoromethylphenyl methane | $CO_2Et$ | H | H,3-$CF_3$ | 70–71° | |
| 8 | 4-Ethoxycarbonylphenoxy-2'-methylphenyl methane | $CO_2Et$ | H | H,2-$CH_3$ | 57–58° | |
| 9 | 4-Ethoxycarbonylphenoxy-3'-methylphenyl methane | $CO_2Et$ | H | H,3-$CH_3$ | | 170°/1 |
| 10 | 4-Ethoxycarbonylphenoxy-4'-methylphenyl methane | $CO_2Et$ | H | H,4-$CH_3$ | 64–65° | |
| 11 | 4-Ethoxycarbonylphenoxy-3',4'-dimethylphenyl methane | $CO_2Et$ | H | H,4-di-$CH_3$ | | 190°/05 |
| 12 | 4-Ethoxycarbonylphenoxy-2',5'-dimethylphenyl methane | $CO_2Et$ | H | 2,5-di-$CH_3$ | 70° | |
| 13 | 4-Ethoxycarbonylphenoxy-4'-ethoxycarbonylphenyl methane | $CO_2Et$ | H | H,4-$CO_2Et$ | 81–3° | |
| 14 | 4-Ethoxycarbonylphenoxy-2'-nitrophenyl methane | $CO_2Et$ | H | H,2$NO_2$ | 98–99° | |
| 15 | 4-Ethoxycarbonylphenoxy-4'-nitrophenyl methane | $CO_2Et$ | H | H,4$NO_2$ | 151–2° | |
| 16 | 4-(Ethoxycarbonylmethyl)phenoxyphenyl methane | $CH_2CO_2Et$ | H | H,H | | 156–8°/0.5 |

| Example No. | Compound | $R_1$ | $R_2$ | $R_3, R_4$ | M.P. (°C) | or B.P. (°C/MM) |
|---|---|---|---|---|---|---|
| 17 | 4-(Ethoxycarbonylmethyl)phenoxy-4'-chlorophenyl methane | $CH_2CO_2Et$ | H | H,4-Cl | 63-4° | |
| 18 | 4-(Methoxycarbonylethyl)phenoxyphenyl methane | $CH_2CH_2-CO_2CH_3$ | H | H,H | 79-81° | |
| 19 | 4-Methyl-phenoxy-phenyl methane | $CH_3$ | H | H,H | 41° | |
| 20 | 4-n-propyl-2-methoxyphenoxyphenyl methane | $n-C_3H_7$ | $OCH_3$ | H,H | 58°-59° | |
| 21 | 4-n-propyl-2-methoxyphenoxy-4'-methylphenyl methane | $n-C_3H_7$ | $OCH_3$ | H,4-$CH_3$ | | 161-2°/0.3 |
| 22 | 4-n-Nonylphenoxy-phenyl methane | $n-C_9H_{19}$ | H | H,H | | 180°/0.4 |
| 23 | 4-n-Dodecylphenoxy-phenyl methane | $n-C_{12}H_{25}$ | H | H,H | | 185°/0.3 |
| 24 | 4-(n-dodecyloxycarbonyl)phenoxy-phenyl methane | $CO_2C_{12}H_{25}$ | H | H,H | 41°-3° | |
| 25 | 4-(n-decyloxycarbonyl)phenoxy phenyl methane | $CO_2C_{10}H_{21}$ | H | H,H | 31° | |
| 26 | 4-(n-hexyloxycarbonyl)phenoxy phenyl methane | $CO_2C_6H_{13}$ | H | H,H | | 200-6°/0.3 |

EXAMPLES 27-28

Using the procedure of Example 1B, the following compounds were prepared in high yield:

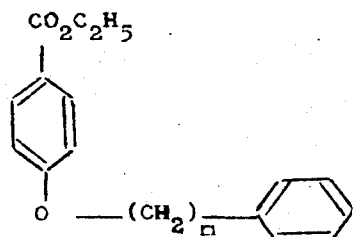

| Ex. No. | Compound | m | b.p.(°C/mm) |
|---|---|---|---|
| 27 | n-1-[4-Ethoxycarbonylphenoxy]-3'-phenyl propane | 3 | 200-6°/0.6 |
| 28 | 1-[4-Ethoxycarbonylphenoxy]-2-phenyl ethane | 2 | 183-6°/0.5 |

EXAMPLES 29-36

The following compounds were synthesised by the general method described in Example 1A. All compounds had spectral characteristics and chemical analyses consistent with the assigned structures. The compounds thus produced are of formula:

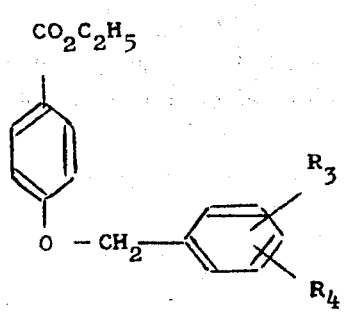

| Ex. No. | Compound | $R_3, R_4$ | m.p. (°C) |
|---|---|---|---|
| 29 | 4-Ethoxycarbonylphenoxy-(3'-nitrophenyl)-methane | H,3-$NO_2$ | 103-5 |
| 30 | 4-Ethoxycarbonylphenoxy-(4'-bromophenyl)methane | H,4-Br | 80 |
| 31 | 4-Ethoxycarbonylphenoxy-(3'-fluorophenyl) methane | H,3-F | 69-70 |
| 32 | 4-(Ethoxycarbonylphenoxy-(2'-methoxyphenyl) methane | H,2-$OCH_3$ | 65 |
| 33 | 4-Ethoxycarbonylphenoxy-(3'-methoxyphenyl) methane | H,2-$OCH_3$ | 56 |
| 34 | 4-Ethoxycarbonylphenoxy-(4'-methoxyphenyl) methane | H,4-$OCH_3$ | 85 |
| 35 | 4-Ethoxycarbonylphenoxy-(2',4'-dichlorophenyl) methane | 2,4-di-Cl | 78 |
| 36 | 4-Ethoxycarbonylphenoxy-(3',4'-dimethoxyphenyl) methane | 3,4-di-$OCH_3$ | 82 |

EXAMPLE 37 n-1 4-Ethoxycarbonylphenoxy - 4 - phenyl - butane was prepared using the procedure 1B, analytically pure by column chromatography.
The precursor 4-phenyl butyl bromide was prepared by standard techniques from 4-phenylbutanol.

EXAMPLES 38-39

The following compounds were prepared from the corresponding substituted 6-phenoxyhexyl bromide:
38. n-1-[4-Ethoxycarbonylphenoxy]-6-[4'-chlorophenoxy]hexane, m.p. 120° - 2°.
39. n-1-[4-Ethoxycarbonylphenoxy]-6-[4'-ethoxycarbonylphenoxy]hexane, m.p. 123° - 5°.

EXAMPLE 40

(4-Methylphenoxy)-benzoyl methane

4-Methylphenol (5.4g; 0.05 m) and potassium carbonate (6.9g; excess) were mixed in dry acetone (40 ml.) phenacyl bromide (9.95 g.; 0.05 m) and added and the mixture was boiled under reflux with vigorous stirring for 4 hours. The mixture was cooled to room temperature, poured into iced water extracted with ether, washed with dilute sodium hydroxide solution water, dried and evaporated. The crude product was recrystallised from ethanol to give the little compound, m.p. 65°C.

EXAMPLES 41-42

By the general procedure of Example 40, the following compounds were prepared:

41. 4-Ethoxycarbonylphenoxy - benzoylmethane, m.p. 116°C 42. 4-Ethoxycarbonylmethylphenoxy - benzoylmethane, m.p. 66°C.

EXAMPLE 43

4-Methylphenylthio - (4'-methylphenyl) methane Sodium (3.45g.; 0.15 m) was dissolved in absolute ethanol (80 ml.), 4-thiophenol (18.6 g; 0.15 m) in absolute ethanol (60 ml.) was added with stirring at room temperature, followed by dropwise addition of α-chloro-4-xylene (21.0g; 0.15 m) in absolute ethanol (60 ml.). The mixture was boiled under reflux for 6 hours with stirring, cooled and added to iced-water. The product was obtained by extraction with ether, drying, evaporating and crystallisation from ethanol m.p. 68°– 9°C.

EXAMPLE 44

By the method of Example 43 was prepared 4-methylphenylthio-phenyl methane, m.p. 67°C.

EXAMPLES 45–50

The following compounds wer prepared by procedure 1A, 1B or that of Example 40.

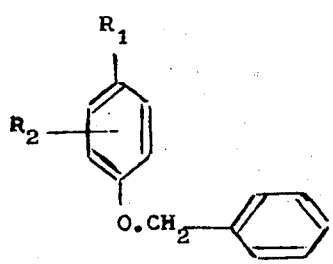

| Example No. | Compound | $R_1$ | $R_2$ | m.p./b.p. | method prepn. |
|---|---|---|---|---|---|
| 45 | 4-Ethylphenoxy-phenyl methane | $C_2H_5$ | H | b.p. 138–46 at 0.5 mm | 1A |
| 46 | 2,4-Dimethylphenoxy-phenyl methane | $CH_3$ | 2-$CH_3$ | b.p. 140–42 at 0.6 mm | 40 |
| 47 | 3,4-Dimethylphenoxy-phenyl methane | $CH_3$ | 3-$CH_3$ | m.p. 35 | 1A |
| 48 | 4-Acetylphenoxy-phenyl methane | $COCH_3$ | H | m.p. 94 | 1B |
| 49 | (2,-Methoxy, 4-formyl phenoxy) phenyl methane | CHO | 2-$OCH_3$ | m.p. 64 | 1A |
| 50 | (2-Methoxy,4-acetyl-phenoxy)-phenyl methane | $COCH_3$ | 2-$OCH_3$ | m.p. 90 | 40 |

EXAMPLES 51–53

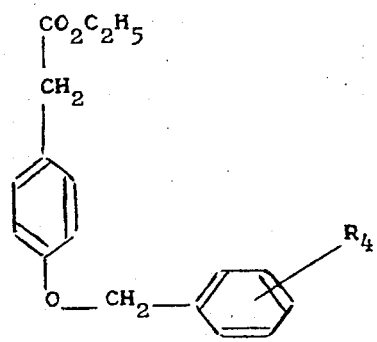

| Example No. | Compound | $R_1$ | m.p. or b.p. | method prepn. |
|---|---|---|---|---|
| 51 | 4-Ethoxycarbonylmethylphenoxy-(2'-fluorophenyl) methane | 2-F | b.p. 180–3 at 0.1 mm | 1A |
| 52 | 4-Ethoxycarbonylmethylphenoxy-(3'-fluorophenyl) methane | 3-F | b.p. 160–3C at 0.3mm | 1A |
| 53 | 4-Ethoxycarbonylmethylphenoxy-(4'-fluorophenyl) methane | 4-F | m.p. 54–5C | 1A |
| 54 | 4-Ethoxycarbonylmethylphenoxy-(2'-methoxyphenyl) methane | 2-$OCH_3$ | b.p. 185–7 at 0.07 mm | 1A |
| 55 | 4'-Ethoxycarbonylmethylphenoxy-(4'-methylphenyl) methane | 4-$CH_3$ | m.p. 37–8C | 1A |

EXAMPLE 56

2- Methoxy, 4-methoxycarbonylphenoxy - phenyl methane

To a solution of thallium trinitrate trihydrate (8.88g) in methanol (40ml.) containing perchloric acid (8 ml. 70%), (2-methoxy-4-acetylphenoxy)-phenyl methane (Example 50) (5.12g) was added in one portion. The mixture was allowed to stir at room temperature for 2 hours, the inorganic salts filtered off and the filtrate diluted with water. The product was extracted into chloroform and after drying (anhyd. Mg $SO_4$) and filtration, the organic solution was passed through a short column of alumina. Evaporation of the eluated gave the crude product which was purified by vacuum distillation, Bp. 200°–210°/2mm. M.p. 48°–50°.

EXAMPLE 57

4 - Carboxyphenoxy - phenyl methane 138 g. (1 mole) of 4-hydroxybenzoic acid was dissolved in 1 liter of 95% ethanol and 500 ml. of 2N sodium hydroxide solution. To this solution was added 346 ml. (3 mole) of benzyl chloride and the mixture was boiled under reflux. 1 liter of 5N sodium hydroxide was added dropwise over a period of 2 hours and the mixture heated a further hour with stirring. The solvent was distilled to half its volume, 2 liters of water added, the warm aqueous solution acidified with hydrochloric acid and the precipitated product recrystallised from 80% ethanol, m.p. 188°C.

EXAMPLES 58–60

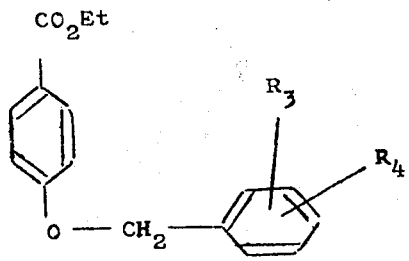

| Example No. | | $R_3,R_4$ | m.p. | method prepn. |
|---|---|---|---|---|
| 58 | 4-Ethoxycarbonylphenoxy-(1'-naphthyl) methane | | 67–9°C | 1A |
| 59 | 4-Ethoxycarbonylphenoxy-(4'-iodophenyl) methane | H,4 - I | 79°C | 1A |
| 60 | 4-Ethoxycarbonylphenoxy-(4'-biphenyl) methane | H,4 - $C_6H_5$ | 132°C | 1A |

EXAMPLE 61

2-Methoxy-4-carboxyphenoxy-phenyl methane

Sodium hydroxide (12g.; 0.3m) was dissolved in 200 ml. of water, silver oxide (11.6g.; 0.05m) added and the resulting mixture warmed to 50°C, 3-methoxy-4-benzyloxybenzaldehyde (12.1g; 0.05m) added in one portion and the mixture heated to 60°C with stirring for 1 hour, stirred 18 hours at room temperature, filtered and acidified to give the acid which was recrystallised from glacial acetic acid, m.p. 172°–3°C.

EXAMPLES 62–73

The following compounds were prepared by the standard condensation (method 1A) of ethyl 4-hydroxybenzoate with ω-phenoxyethyl bromides in sodium ethoxide/ethanol. The required intermediate ω-phenoxyethyl bromides were prepared from ω-dibromoethanes and the corresponding phenols in refluxing sodium hydroxide solution (of E. W. Littmann and C. S. Marvel., J. Amer. Chem. Soc., 52 (1930) 287)

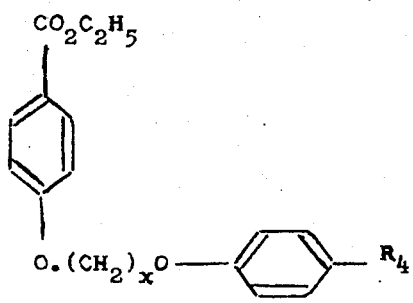

| Ex. No. | Compound | x | $R_4$ | m.p. |
|---|---|---|---|---|
| 62 | 4-Ethoxycarbonylphenoxy-(4'-chlorophenoxy) methane | 1 | Cl | 58°C |
| 63 | 1-(4-Ethoxycarbonylphenoxy)-2-(4'chlorophenoxy)ethane | 2 | Cl | 72–4°C |
| 64 | n-1-(4-Ethoxycarbonylphenoxy-3-(4'-chlorophenoxy) propane | 3 | Cl | 52–3°C |
| 65 | n-1-(4-Ethoxycarbonylphenoxy)-4-(4'-chlorophenoxy) butane | 4 | Cl | 75–6° |
| 66 | n-1-(4-Ethoxycarbonylphenoxy)-5-(4'-chlorophenoxy) pentane | 5 | Cl | 86°C |
| 67 | n-1-(4-Ethoxycarbonylphenoxy)-4-(4'-methylphenoxy) butane | 4 | $CH_3$ | 89–90°C |
| 68 | n-1-(4-Ethoxycarbonylphenoxy)-5-(4'-methylphenoxy) pentane | 5 | $CH_3$ | 82–4°C |
| 69 | n-1-(4-Ethoxycarbonylphenoxy)-6-(4'-methylphenoxy) hexane | 6 | $CH_3$ | 117°C |
| 70 | 1-(4-Ethoxycarbonylphenoxy)-2-phenoxy ethane | 2 | H | 79°C |
| 71 | n-1-(4-Ethoxycarbonylphenoxy)-4-phenoxy butane | 4 | H | 54°C |
| 72 | n-1-(4-Ethoxycarbonylphenoxy)-5-phenoxy pentane | 5 | H | 60°C |
| 73 | n-1-(4-Ethoxycarbonylphenoxy)-6-phenoxy hexane | 6 | H | 68–9°C |

EXAMPLE 74

1-(4-Ethoxycarbonylphenoxy)-2-phenylthio ethane

This compound was prepared by the condensation procedure 1A. The required intermediate 2-bromoethylphenyl sulphide may be prepared by condensing 1,2-bromoethane and thiophenol in sodium hydroxide solution, in a manner analogous to that used for preparation of the intermediates for compounds of Example Nos. 62–73, but a method which gives better yields uses the scheme:

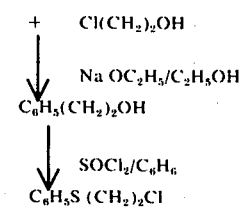

Condensation with ethyl 4-hydroxybenzoate gave 1-(4-ethoxycarbonylphenoxy)-2-phenylthio ethane, m.p. 50°–51°C.

EXAMPLES 75–78

These compounds were prepared by the procedure 1A:

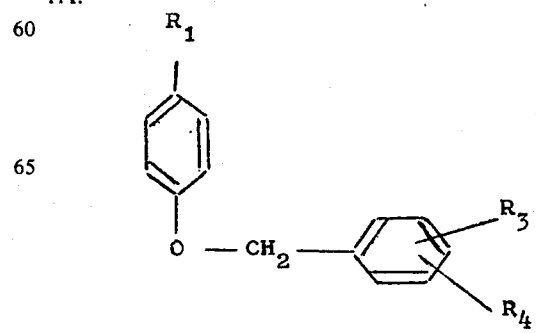

| Example No. | Compound | $R_1$ | $R_3,R_4$ | m.p. |
|---|---|---|---|---|
| 75 | 4-Cyanophenoxy-(4'-fluorophenyl) methane | CN | H,4-F | 118–9°C |
| 76 | 4-Cyanophenoxy-(3',4-dichlorophenyl) methane | CN | 3,4-di-Cl | 114°C |
| 77 | 4-Cyanophenoxy-(4'-methylphenyl) | CN | H,4-Me | 113–4°C |
| 78 | 4-Formylphenoxy-(4'-fluorophenyl) | CHO | H,4-F | 98°C |

EXAMPLE 79

4-Carboxyphenoxy-(3,4'-dichlorophenyl) methane

4-Cyanophenoxy-(3,4-dichlorophenyl) methane (11.12g.; 0.04 m) was dissolved in ethanol (100 ml.), 10N sodium hydroxide (100 ml.) was added and the mixture boiled under reflux 24 hours with vigorous stirring. The mixture was cooled, filtered and the sodium salt of the acid thus obtained was boiled under reflux with concentrated hydrochloric acid (100 ml.) for 6 hours, cooled, filtered and the product recrystallised from 5:1 acetic acid-ethanol to give the title compound, m.p. 222°–3°C.

EXAMPLE 80

Prepared by the same method of Example 79 was 4-Carboxyphenoxy-(4'-methylphenyl) methane, m.p. 219°C.

EXAMPLE 81–82

The two compounds below were prepared by method 1A, the intermediate p-(ethoxycarbonylalkylene) phenols being prepared by the method of Papa et al J. Amer. Chem. Soc. 69, 3018 (1947)

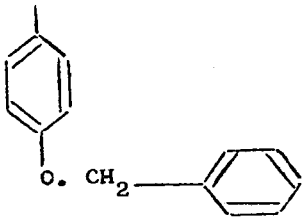

| Example No. | Compound | q |
|---|---|---|
| 81 | 4-Ethoxycarbonylpentylenephenoxy-phenyl methane | 5 } analytically pure by column chromatography |
| 82 | 4-Ethoxycarbonyloctylenephenoxy-phenyl methane | 8 |

EXAMPLE 83

4-Cyclopentyloxycarbonylphenoxy-phenyl methane

Cyclopentanol (2.58g.; 0.03 m) was dissolved in pyridine (50 ml), 4-benzyloxybenzoyl chloride (6.76g; 0.03 m) was added and the mixture was boiled under reflux 6 hours. The resulting mixture was added to iced-water, extracted with ether, the organic extract washed with 2×100 ml. of 2N hydrochloric acid, 2×100 ml. saturated sodium bicarbonate solution and 1×100 ml. of water, dried (MgSO$_4$) and evaporated. The ester was purified by elution from a column of silica in toluene.

EXAMPLE 84

4-Methoxycarbonylphenoxy-phenyl methane

4-Hydroxybenzoic acid (10 g) was dissolved in methanol (200 ml.), concentrated sulphuric acid (2 ml.) was added and the mixture boiled under reflux for 18 hours. The resulting mixture was poured into iced water, extracted with 2×100 ml. of diethyl ether, washed with 2×100 ml. saturated sodium bicarbonate solution, 1×100 ml. of water, dried and evaporated to give methyl 4-hydroxybenzoate. The phenolic ester was benzylated using method 1A to give the title compound, m.p. 99°C.

EXAMPLES 85–89

The following compounds were prepared by the method of Example 83 or 84:

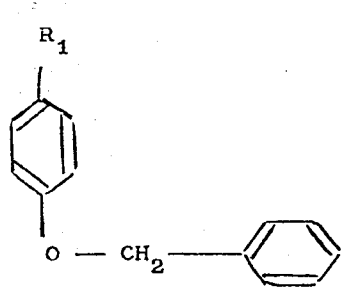

| Example No. | Compound | $R_1$ | m.p. | Method of Ex. No. |
|---|---|---|---|---|
| 85 | 4-n-Butoxycarbonylphenoxy-phenyl methane | $CO_2C_4H_9$ (n) | * | 83 |
| 86 | 4-Benzyloxycarbonylphenoxy-phenyl methane | $CO_2CH_2C_6H_5$ | * | 83 |
| 87 | 4-(Ethoxyethoxycarbonyl)phenoxy-phenyl methane | $CO_2(CH_2)_2OC_2H_5$ | * | 84 |
| 88 | 4-iso-propoxycarbonylphenoxy-phenyl methane | $CO_2CH(CH_3)_2$ | 62–3° | 83 |
| 89 | 4(2-Dimethylaminoethoxycarbonyl) phenoxy-phenyl methane | $CO_2(CH_2)_2N(CH_3)_2$ | * | 83 |

*analytically pure by column chromatography

EXAMPLES 90–95

The following compounds were prepared by the procedure 1A:

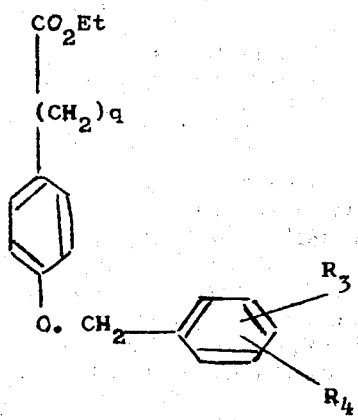

| Example No. | Compound | g | $R_3, R_4$ | b.p. |
|---|---|---|---|---|
| 90 | 4-(2-Ethoxycarbonylethyl)-phenoxy-(2'-fluorophenyl) methane | 2 | H,2-F | oil* |
| 91 | 4-(2-Ethoxycarbonylethyl)-phenoxy-(3'-fluorophenyl) methane | 2 | H,3-F | oil* |
| 92 | 4-(2-Ethoxycarbonylethyl)-phenoxy-(4'-fluorophenyl) methane | 2 | H,4-F | oil* |
| 93 | 4-(Ethoxycarbonylmethyl)-phenoxy-(2',3'-dimethoxyphenyl) methane | 1 | 2-OCH₃, 3-OCH₃ | 224–5°C/1.5 mm |
| 94 | 4-(2-Ethoxycarbonylethyl)-phenoxy-(2',3'-dimethoxyphenyl) methane | 2 | 2-OCH₃, 3-OCH₃ | 232–4°C/1.5 mm |
| 95 | 4-(3-Ethoxycarbonyl(n)-propyl)-phenoxy phenyl methane | 3 | H,H | oil* |

*compound purified by chromatography and spectral information consistent with assigned structure.

EXAMPLE 96

4-(4-Ethoxycarbonyl-(n)-butylcarbonyl) phenoxy(4'-methylphenyl) methane

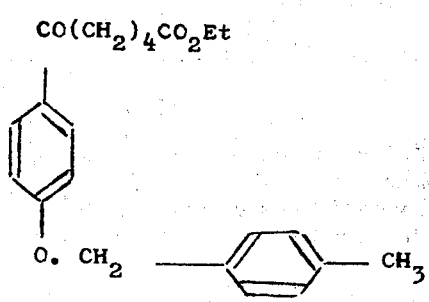

To a stirred solution of phenoxy-(4-methylphenyl) methane (8.7g.; 0.05 mole) in tetrachloroethane (40ml) at −5 to 0°C, aluminum chloride (8.0g.; 0.06 mole) was added portionwise. To this mixture ethyl adipoyl chloride (9.6g.; 0.05 mole) was added dropwise with stirring at such a rate that the temperature did not rise above 0°, and stirring continued for a further 3hr. maintaining the temperature of the mixture at 0°. The reaction mixture was allowed to warm to room temperature overnight then the solvent removed by steam distillation. Extraction of the aqueous residue with ether, yielded after drying (anhyd. MgSO₄) and removal of solvent 15.66g. of crude product which was purified by distillation (b.p. 228°–245°/2mm) and column chromatography.

EXAMPLE 97

Prepared by the same method of Example 96 was 4-(7-methoxycarbonyl-(n)-heptyl-carbonyl)phenoxy (4'-methylphenyl) methane, as an oil purified by chromatography and having spectral information consistent with the assigned structure.

| Example No. | Compound | $R_3, R_4$ | m.p.(°C) |
|---|---|---|---|
| 98 | 4-Ethoxycarbonylphenyl-(4'-methylphenoxy)-methane | H,4-CH₃ | 58° |
| 99 | 4-Ethoxycarbonylphenyl-(4'-chlorophenoxy)-methane | H,4-Cl | 66–7° |
| 100 | 4-Ethoxycarbonylphenyl-(4'-bromophenoxy)-methane | H,4-Br | 79° |
| 101 | 4-Ethoxycarbonylphenyl-(4'-cyanophenoxy)-methane | H,4-CN | 97° |
| 102 | 4-Ethoxycarbonylphenyl-(3',4'-dimethylphenoxy)-methane | 3-CH₃,4-CH₃ | 60° |
| 103 | 4-Ethoxycarbonylphenyl-(2',4'-dimethylphenoxy)-methane | 2-CH₃,4-CH₃ | 49° |
| 104 | 4-Ethoxycarbonylphenyl-(4'-methoxyphenoxy)-methane | H,4-OCH₃ | 68° |
| 105 | 4-Ethoxycarbonylphenyl-(4'-fluorophenoxy)-methane | H,4-F | 55° |
| 106 | (4-Ethoxycarbonylphenyl)-phenoxymethane | H,H | 57–8° |

EXAMPLES 98–106

The following compounds were prepared by procedure 1A:

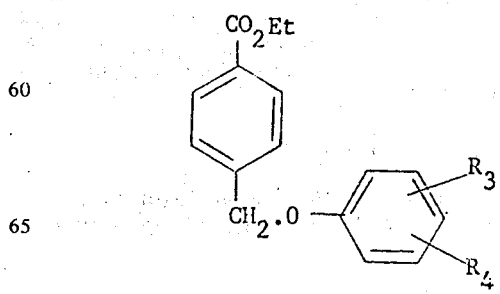

EXAMPLE 107

4-Aminocarbonylphenoxy-phenyl methane

A mixture of 4-cyanophenoxy phenyl methane (10.45g.; 0.05 mole), 30% hydrogen peroxide (20ml) and 6N NaOH (20ml) and ethanol (30ml) was maintained at 40°–50° for 3 hrs., cooled and neutralised. The product was filtered off and recrystallised from ethanol M.p. 186°–7°.

EXAMPLE 108

4-(N-cyclohexylaminocarbonyl-phenoxy phenyl methane

A mixture of cyclohexylamine (3.6g.; 0.036 mole) and 4-chlorocarbonylphenoxy phenyl methane (9.04g.; 0.037 mole) in pyridine were heated under reflux for 6hr., then poured into water. The product was extracted into dichloromethane, the organic layer washed with dil. HCl and dried (anhyd. MgSO$_4$). Removal of the drying agent and solvent yielded the crude product which was recrystallised from ethanol M.p. 183°–4°.

EXAMPLES 109–111

The following compounds were prepared by the same method of Example 108:

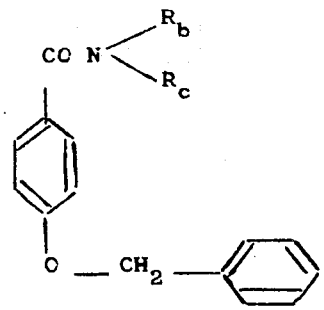

| Example No. | Compound | $R_b$,$R_c$ | m.p.(°C) |
|---|---|---|---|
| 109 | 4-(N-laurylaminocarbonyl)-phenoxy phenyl methane | H,—(CH$_2$)$_{11}$CH$_3$ | 114–5° |
| 110 | 4-(N-cetylaminocarbonyl)-phenoxy phenyl methane | H,—(CH$_2$)$_{15}$CH$_3$ | 120° |
| 111 | 4-(N,N-diethylaminocarbonyl)-phenoxy phenyl methane | C$_2$H$_5$,C$_2$H$_5$ | 63–4° |

EXAMPLE 112

Sodium 4-carboxyphenoxy phenyl methane

To a solution of 4-ethoxycarbonylphenoxy phenyl methane (6.3g) in ethanol (30ml), sodium hydroxide solution (70ml.; 10N) was added and the mixture boiled under reflux with vigorous stirring for 18 hr. After cooling the sodium salt was filtered off and dried, m.p. >340°.

EXAMPLE 113

Potassium 4-carboxyphenoxy phenyl methane

A mixture of 4-carboxyphenoxy phenyl methane (5.7g.; 0.025 mole) and potassium hydroxide (1.4g.; 0.025 mole) in water (40ml) were heated at reflux for 1 hr., on cooling the potassium salt was filtered off and dried, m.p. >340°.

EXAMPLE 114

By the procedure of Example 113 was prepared calcium 4-carboxyphenoxy phenyl methane, m.p. >340°.

EXAMPLE 115

4-Carboxyphenoxy-(2'-methoxyphenyl) methane

4-Ethoxycarbonylphenoxy-(2'-methoxyphenyl) methane (14.3g.; 0.05 mole) in sodium hydroxide (100ml.; 10N) was heated under reflux with vigorous stirring for 18 hr. The mixture was then cooled, filtered and the sodium salt converted to the acid by refluxing with hydrochloric acid (6N) for 3 hours. The product was filtered off and recrystallised from acetic acid M.p. 181°–2°.

EXAMPLE 116

Prepared by the procedure of Example 115 was 4-carboxyphenoxy-(4'-fluorophenyl) methane.

EXAMPLES 117–118

The following compounds were prepared by the procedure 1A:

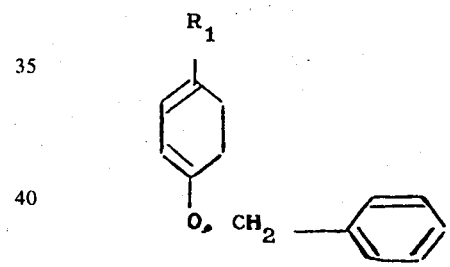

| Example No. | Compound | R$_1$ | m.p.(°C) |
|---|---|---|---|
| 117 | 4-Cyanophenoxy phenyl methane | CN | 96° |
| 118 | 4-Hydroxymethylphenoxy phenyl methane | CH$_2$OH | 84–5° |
| 119 | 4-Phenoxycarbonylphenoxy phenyl methane | CO$_2$C$_6$H$_5$ | 136–7° |

EXAMPLE 120

2,3-Acetonide of glycerylcarbonylphenoxy phenyl methane

To a solution of glycerol-2,3-acetonide (13.2g.; 0.1 mole) in pyridine (100ml), 4-chlorocarbonylphenoxy phenyl methane (24.6g.; 0.1 mole) was added and the mixture boiled under reflux for 18 hr. The mixture was then poured into icewater and extracted with ether, the organic layer was washed well with dilute hydrochloric acid, water and dried (anhyd. MgSO$_4$). Removal of the drying agent and solvent gave the crude product which was recrystallised from ethanol to yield 15.30 g., m.p. 88°C.

EXAMPLES 121–131

Examples 121 – 131 illustrate alternative methods of preparation of some of the compounds of the invention.

EXAMPLE 121

Preparation of 4-ethoxycarbonylphenoxy phenyl methane from ethyl 4-hydroxybenzoate and a benzyl halide in the presence of an organic base A solution of ethyl 4-hydroxybenzoate (8.3g; 0.05 mole) and benzyl chloride (6.3g.; 0.05 mole) in pyridine (50ml) and was boiled under reflux overnight, to yield after standard purification methods, the product, identified by GLC using a 3% OV-17 column at 220°C.

EXAMPLE 122

Preparation of 4-ethoxycarbonylphenoxy phenyl methane using an organo-metallic derivative of 4-benzyloxybenzene To a solution of methyl magnesium iodide prepared from magnesium (0.72g.; 0.03 mole) and methyl iodide (1.42g.; 0.01 mole) in ether (20ml) using standard methods, 4-bromo-phenylbenzyl ether in ether (20ml) was added dropwise with stirring then stirred until reaction was complete (1hr.). Ethyl chloroformate (3.24g.; 0.03 mole) in dry ether (20ml) was then added to the reaction mixture which was then boiled under reflux for 2 hrs. After cooling the reaction mixture was allowed to stand at room temperature for two days then worked up by the addition of water (40ml) and dilute hydrochloric acid (20ml). Separation of the ether layer followed by drying (anhyd. MgSO$_4$), yielded 4-ethoxycarbonylphenoxy phenyl methane, m.p. 45°C.

EXAMPLE 123

Preparation of 4-carboxyphenoxy phenyl methane via Grignard Reagent

The Grignard derivative of 4-bromophenoxy phenyl methane prepared as in the previous example was poured onto dry, solid carbon dioxide. The mixture was allowed to warm to room temperature then after acidification yielded 4-carboxyphenoxy phenyl methane.

EXAMPLE 124

Esterification of 4-carboxyphenoxy phenyl methane a. 4-Carboxyphenoxy phenyl methane (20g) in ethanol (250ml) containing concentrated sulphuric acid (2.5ml) was boiled under reflux for 24 hrs. The ethanol was removed under reduced pressure and the residue taken up in ether and washed well with water and sodium bicarbonate solution. After drying (anhyd. MgSO$_4$) and removal of the solvent gave ethoxycarbonylphenoxy phenyl methane which was purified by recrystallisation from petrol, m.p. 45°C.

b. 4-Carboxyphenoxy phenyl methane (20g) was converted to the acid chloride by heating under reflux with thionyl chloride for 1hr. Excess thionyl chloride was removed by distillation to yield 4-chlorocarbonylphenoxy phenyl methane.

A mixture of 4-chlorocarbonylphenoxy phenyl methane (12.3g.; 0.05 mole), propan-2-ol (3.6g.; 0.6 mole), pyridine (5g) and xylene (50ml) were boiled under reflux for 18hr. The cooled mixture was poured into water and extracted with dichloromethane. The organic extract was washed well with water and dried (anhyd. MgSO$_4$), filtration and evaporation yielded 4-isopropoxycarbonylphenoxy phenyl methane, m.p. 62°–3°C.

EXAMPLE 125

4-Ethoxycarbonylphenoxy phenyl methane from 4-methoxycarbonylphenoxy phenyl methane To a solution of sodium (0.1g) in ethanol (100ml) 4-methoxycarbonylphenoxy phenyl methane (2g) was added and the mixture heated under reflux for 4 hr. The mixture was cooled, poured into water and extracted with ether. The other solution was dried (anhyd. MgSO$_4$) and evaporated to yield 4-ethoxycarbonylphenoxy phenyl methane, m.p. 45°C.

EXAMPLE 126

Preparation of 4-ethoxycarbonylphenoxy phenyl methane from benzyl alcohol and ethyl 4-hydroxybenzoate Benzyl alcohol (2.70g.; 0.025 mole) was added to a solution of ethyl 4-hydroxybenzoate (4.15g.; 0.025 mole) in dry ether followed by the careful addition of phosphorus pentachloride (2.5g). The mixture was boiled under reflux for 24 hrs. then poured into water and the ether layer removed. The aqueous solution was extracted with ether and the combined organic extracts dried (anhyd. MgSO$_4$) to yield, on evaporation and purification by chromatography, 4-ethoxycarbonylphenoxy phenyl methane, m.p. 45°C.

EXAMPLE 127

Reaction of ethyl 4-diazobenzoate with benzyl alcohol

Ethyl 4-aminobenzoate (8.25g) in a mixture of conc. hydrochloric acid (12.5ml) and water 12.5ml.) at 0°C was diazotised by the addition of sodium nitrite (3.45g). The solution of the diazo compound was added to benzyl alcohol (20g) at 35°C with stirring then stirred at this temperature for 3hr. The reaction mixture was cooled and 4-ethoxycarbonylphenoxy phenyl methane isolated by extraction with ether, m.p. 45°C.

EXAMPLE 128

Reaction of ethyl 4-hydroxybenzoate and dimethyl formamide dibenzyl acetal

A mixture of ethyl 4-hydroxybenzoate (12.3g.; 0.074 mole) and dimethyl formamide dibenzyl acetal (20g.; 0.074 mole) in ethylene dichloride (500ml) was boiled under reflux for 2 hrs. Removal of the solvent yielded 37.04g. crude product from which 4-ethoxycarbonylphenoxy phenyl methane was obtained by chromatography, m.p. 45°C.

EXAMPLE 129

Preparation of 4-ethoxycarbonylphenoxy-(4'-fluorophenyl) methane by hydrolysis of an imino ether A solution of 4-cyanophenoxy-(4'-fluorophenyl) methane (2.25g.; 0.1 mole) in dry ether (20ml) with ethanol (0.46g.; 0.1 mole) was cooled in a ice-bath and then saturated with dry hydrogen chloride gas then allowed to stand for 24 hrs. The resulting solid was filtered off and dried, m.p. 210°C (rearrangement at 135°C).

The imino-ether (1.54g) was dissolved in water (30ml) neutralised with dilute sodium hydroxide solution then boiled under reflux for 3 hrs. Mixture cooled and the product extracted with ether to give 4-ethoxycarbonylphenoxy-(4'-fluorophenyl) methane m.p. 60°-2°C.

EXAMPLE 130 a. Oxidation of 4-hydroxymethylphenoxy phenyl methane to 4-formylphenoxy phenyl methane A mixture of 4-hydroxymethylphenoxy phenyl methane (1.07g.; 0.005 mole) and active manganese dioxide (0.44g.; 0.005 mole) in dry acetone (20ml) was stirred under dry nitrogen for 18 hrs. at room temperature. The inorganic salts were then filtered off to yield 4-formylphenoxy phenyl methane identified by TLC.

b. Oxidation of 4-acetylphenoxy phenyl methane to 4-carboxyphenoxy phenyl methane 4-Acetylphenoxy phenyl methane (0.30g) in dioxan (20ml), water was added (1ml) followed by sodium hydroxide (2ml. 2N) then dropwise addition of a solution (35ml) prepared from potassium iodide (20g) and iodine (10g) in water (100ml). The mixture was acidified, decolourised with sodium dithionite and filtered. The material on the filter was washed with dichloromethane and identified as 4-carboxyphenoxy phenyl methane, m.p. 187°-8°C.

c. Hydrolysis of 4-aminocarbonylphenoxy phenyl methane to 4-carboxyphenoxy phenyl methane A mixture of 4-aminocarbonylphenoxy phenyl methane (10g) in ethanol (100ml) and sodium hydroxide (100ml., 10N) was heated under reflux with vigorous stirring for 24hrs. The reaction mixture was cooled, the precipitated sodium salt was filtered off washed with a little water then converted to 4-carboxyphenoxy phenyl methane by boiling under reflux with concentrated hydrochloric acid (100ml) for 6hr. Dilution of the cooled mixture and extraction with ether yielded 4-carboxyphenoxy phenyl methane, m.p. 188°.

d. Oxidation of 4-methylphenoxy phenyl methane to 4-carboxyphenoxy phenyl methane A mixture of 4-methylphenoxy phenyl methane (2g) was suspended in aqueous sodium dichromate solution (20ml. 50%) and concentrated sulphuric acid (10ml) added dropwise with stirring. The mixture was stirred at room temperature overnight then warmed on a water bath for 1hr. The mixture was cooled, diluted with water and the 4-carboxyphenoxy phenyl methane (m.p. 188°) isolated with ether.

EXAMPLE 131

Preparation of 4-ethoxycarbonylphenoxy phenyl methane from ethyl 4-hydroxybenzoate and the tosylate of benzyl alcohol To a solution of sodium (0.23g) in ethanol (25ml) was added the p-toluenesulphonate of benzyl alcohol (2.62g) in ethanol (25ml) and the mixture boiled under reflux for 2 hrs. The reaction mixture was diluted with sodium bicarbonate solution and 4-ethoxycarbonylphenoxy, phenyl methane isolated by extraction with ether, m.p. 45°C.

Biological Data

The hypocholesterolaemic and/or hypotriglyceridaemic and/or blood glucose lowering effects of several compounds of the present invention were demonstrated in the following experiment:

a. Hypolipidaemic Results

Groups of 8 male albino rats (C.F.Y. strain), weighing approximately 150 g. were given a powdered commercially available diet (oxoid) to which compounds were added at level of 0.25%. These diets were fed for seven days. The rats were then killed and their serum total cholesterol and triglyceride were measured by the Technicon Autoanalyser.

Table 1 shows the results expressed in terms of percentage cholesterol lowering and percentage triglyceride lowering compared with control.

b. Hypoglycaemic Results (alloxanised mice)

Groups of 18 mice were given an I.V. dose of 100MG/KG alloxan each. At 5-7 days after dosing, groups of six mice were dosed with 300 MG/KG of drug (The remaining 12 acting as a control group). The drug-dosed mice were bled from the tail vein at 2 and 4 hours after dosing and glucose measured using glucose oxidase peroxidase by the Technicon Autoanalyser. The results were expressed as blood glucose lowering against control and are shown in table 1 according to the following scale:

TABLE 1

| Compound of Example No. | % change from control of | | Blood glucose scale |
|---|---|---|---|
| | (a) Serum Cholesterol | (b) Serum Triglyceride | |
| 1 | 12 | 53 | 3 |
| 2 | 26 | 43 | 3 |
| 3 | 19 | 0 | 0 |
| 4 | 25 | 55 | — |
| 5 | 0 | 0 | |
| 6 | 30 | 48 | 0 |
| 7 | 11 | 0 | 1 |
| 8 | 0 | 58 | 0 |
| 9 | 0 | 58 | 1 |
| 10 | 18 | 54 | 3 |
| 11 | 19 | 47 | 0 |
| 12 | −13 | 47 | 0 |
| 13 | 0 | 53 | |
| 14 | 20 | 21 | 0 |
| 15 | 12 | 0 | 0 |
| 16 | 18 | 84 | |
| 17 | 28 | 91 | |
| 18 | 15 | 45 | |
| 19 | 19 | 0 | 3 |
| 20 | 15 | 0 | |
| 21 | 13 | 0 | |
| 22 | 0 | 67 | |
| 23 | 0 | 37 | |
| 24 | −11 | −57* | |
| 25 | −9 | −64* | |
| 26 | −9 | −64* | |
| 27 | −25* | −34* | |
| 28 | −19 | −42* | |
| 29 | −7 | −28 | |
| 30 | −29* | −52* | |
| 31 | −19* | −60* | |
| 32 | −13* | −42* | |
| 33 | −10 | −32* | |
| 34 | −7 | −55* | |
| 35 | −18 | −42* | |
| 36 | −1 | −33* | |
| 37 | −38* | −74* | |
| 38 | −21* | −67*. | |
| 39 | 0 | −64 | |
| 40 | +9 | −28* | |
| 41 | 0 | −13 | |
| 42 | 0 | −10 | |
| 43 | −18* | −35* | |
| 44 | −7 | −35* | |
| 45 | −17* | −57* | |
| 46 | −34* | −49* | |
| 47 | −3 | −62 | |
| 48 | +9 | −46 | |
| 49 | −23* | −18 | |
| 50 | +5 | −51* | |

TABLE 1-continued

| Compound of Example No. | % change from control of (a) Serum Cholesterol | (b) Serum Triglyceride | Blood glucose scale |
|---|---|---|---|
| 51 | −29* | −64* | |
| 52 | −37* | −71 | |
| 53 | −29* | −71 | |
| 54 | −24* | −57* | |
| 55 | −45* | −68* | |
| 56 | −30* | −45* | |
| 57 | −23* | −65* | |
| 58 | −4 | −68* | |
| 59 | −18* | −60* | |
| 61 | 0 | −28* | |
| 62 | −13 | −50* | |
| 63 | −16* | −61* | |
| 64 | −30* | −52* | |
| 65 | −30* | −64* | |
| 66 | −25* | −53* | |
| 67 | −17* | −29 | |
| 68 | −15* | −12 | |
| 69 | −4 | +14 | |
| 70 | −17* | −67 | |
| 71 | −13 | −66 | |
| 72 | −22* | −58 | |
| 73 | −8 | −46* | |
| 74 | −14* | −55* | |
| 75 | −17* | +1 | |
| 76 | −19* | −6 | |
| 77 | −19* | −58* | |
| 78 | −15 | −59* | |
| 79 | −9 | −20 | |
| 80 | −10 | −57* | |
| 81 | −38* | −83* | |
| 82 | −9 | −43 | |
| 83 | −14 | −29* | |
| 84 | −19* | −51* | |
| 85 | −10 | −47* | |
| 86 | −21 | −50 | |
| 87 | −17 | −51* | |
| 88 | −10* | −40* | |
| 98 | −20* | −42* | |
| 99 | −13* | +79* | |
| 100 | −6 | −16 | |
| 101 | −12 | −21* | |
| 102 | +3 | +110 | |
| 103 | 0 | 0 | |
| 104 | 0 | −57* | |
| 105 | −14 | −50* | |
| 106 | −25* | −38* | |
| 107 | −1 | −63* | |
| 108 | −5 | −18 | |
| 109 | +1 | −11 | |
| 110 | +11 | −43* | |
| 113 | −20* | −57* | |
| 115 | −29* | +71* | |
| 117 | +7 | −31* | |
| 118 | −3 | −45* | |

Scale:
0 = 0 - 10% lowering
1 = 10 - 20% lowering
2 = 20 - 30% lowering
3 = 30 - 40% lowering
4 = > 40% lowering

We claim:

1. A compound selected from the group consisting of a compound of the formula:

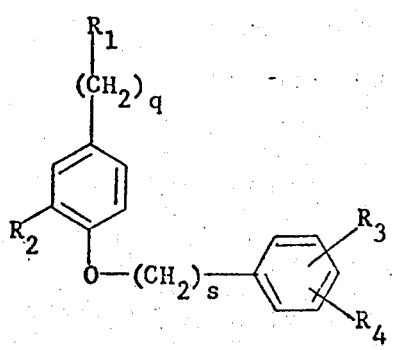

wherein:
$R_1$ is carboxylic acid ester converted in the human body to a carboxylic acid group;
$R_2$ is hydrogen, lower alkyl or lower alkoxyl;
$R_3$ is hydrogen, halogen, lower alkyl or lower alkoxyl;
$R_4$ is hydrogen, halogen, phenyl, lower alkyl, lower alkoxyl, halo-lower alkyl, nitro, or a carboxylic ester group; or $R_3$ and $R_4$ together form the residue of a benzene ring;
q is zero or an integer from 1 to 12; and
s is an integer from 2 to 6; and a compound of the formula:

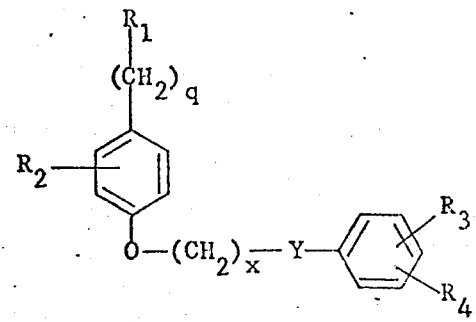

wherein:
$R_1$ is a carboxylic acid ester converted in the human body to a carboxylic acid group;
$R_2$ is hydrogen, lower alkyl or lower alkoxyl;
$R_3$ is hydrogen, halogen, lower alkyl or lower alkoxyl; and
$R_4$ is halogen, phenyl, lower alkyl, lower alkoxy, halo-lower alkyl, nitro or a carboxylic ester group; or $R_3$ is halogen, lower alkyl or lower alkoxyl; and $R_4$ is hydrogen, halogen, phenyl, lower alkyl, lower alkoxyl, halo-lower alkyl, nitro or a carboxylic ester group; or $R_3$ and $R_4$ together form the residue of a benzene ring;
q is zero or an integer from 1 to 12;
x is an integer from 1 to 6; and
Y is oxygen.

2. A compound according to claim 1 of the formula:

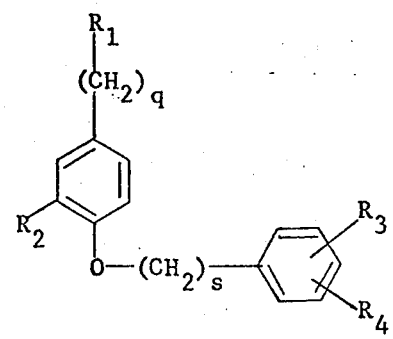

wherein:
$R_1$ is a carboxylic acid ester converted in the human body to a carboxylic acid group;
$R_2$ is hydrogen, lower alkyl or lower alkoxyl;
$R_3$ is hydrogen, halogen, lower alkyl or lower alkoxyl;
$R_4$ is hydrogen, halogen, phenyl, lower alkyl, lower alkoxyl, halo-lower alkyl, nitro, or a carboxylic ester group; or $R_3$ and $R_4$ together form the residue of a benzene ring;
q is zero or an integer from 1 to 12; and
s is an integer from 2 to 6.

3. A compound according to claim 1 of the formula:

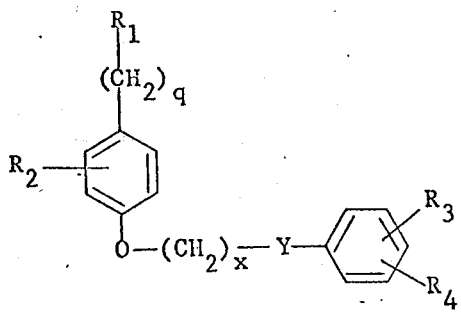

wherein:
R₁ is a carboxylic acid ester converted in the human body to a carboxylic acid group;
R₂ is hydrogen, lower alkyl or lower alkoxyl;
R₃ is hydrogen, halogen, lower alkyl or lower alkoxyl; and
R₄ is halogen, phenyl, lower alkyl, lower alkoxyl, halo-lower alkyl, nitro or a carboxylic ester group; or R₃ is halogen, lower alkyl or lower alkoxyl; and R₄ is hydrogen, halogen, phenyl, lower alkyl, lower alkoxyl, halo-lower alkyl, nitro or a carboxylic ester group; or R₃ and R₄ together form the residue of a benzene ring;
q is zero or an integer from 1 to 12;
x is an integer from 1 to 6; and
Y is oxygen.

4. A compound according to claim 3 wherein Q is O, and R₂ is hydrogen.
5. A compound according to claim 3 wherein x is 6.
6. The compound according to claim 5 which is: n-1-[4-ethoxycarbonylphenoxy]-6-[4'-chlorophenoxy]hexane of the formula:

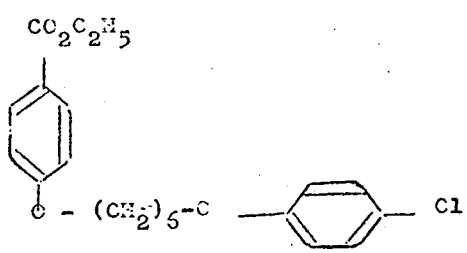

7. A compound according to claim 2 of the formula:

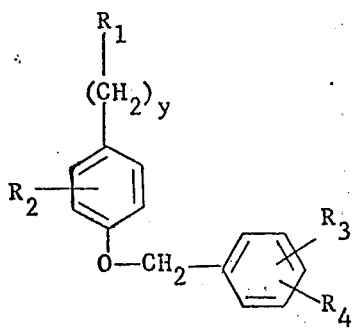

wherein:
R₁ is a carboxylic acid ester converted in the human body to a carboxylic acid group;
R₂ is hydrogen, lower alkyl or lower alkoxyl;
R₃ is hydrogen, halogen, lower alkyl or lower alkoxyl;

R₄ is hydrogen, halogen, phenyl, lower alkyl, lower alkoxyl, halo-lower alkyl, nitro or a carboxylic ester group; and
y is an integer from 1 to 12.

8. A compound according to claim 7 wherein R₂ is hydrogen.
9. A compound according to claim 8 wherein R₃ is hydrogen and R₄ is lower alkoxyl.
10. A compound according to claim 9 which is 4-(ethoxycarbonylmethyl) phenoxy-(2'-methoxyphenyl) methane of formula:

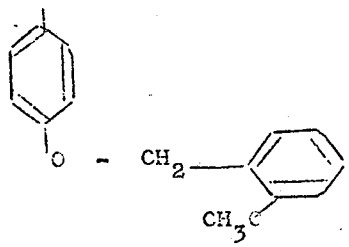

11. A compound according to claim 1 of the formula:

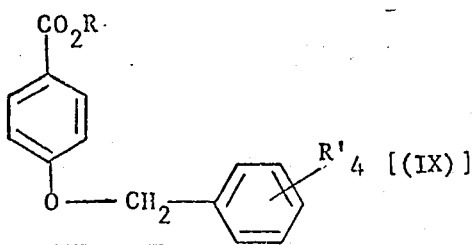

wherein R is lower alkyl, and R₄' is fluorine, bromine, iodine or 4-methyl.

12. A compound according to claim 1 wherein R₄ is halogen.
13. A compound according to claim 1 wherein R₄ is phenyl.
14. A compound according to claim 1 wherein R₄ is lower alkyl.
15. A compound according to claim 1 wherein R₄ is lower alkoxyl.
16. A compound according to claim 1 wherein R₄ is halo lower alkyl.
17. A compound according to claim 1 wherein R₄ is nitro.
18. A compound according to claim 1 wherein R₄ is a carboxylic ester group.
19. A compound according to claim 1 wherein R₃ and R₄ together form the residue of a benzene ring.
20. The compound according to claim 11 which is 4-ethoxycarbonylphenoxy-(4'-bromophenyl) methane.
21. The compound according to claim 11 which is 4-ethoxycarbonylphenoxy-(4'-methylphenyl) methane.
22. The compound according to claim 11 which is 4-ethoxycarbonylphenoxy-(4'-fluorophenyl) methane.

* * * * *

UNITED STATES PATENT AND TRADEMARK OFFICE
CERTIFICATE OF CORRECTION

PATENT NO. : 3,983,164
DATED : Sept. 28, 1976
INVENTOR(S) : David Edward Thorne, Keith Howard Baggaley, Brian Morgan.

It is certified that error appears in the above-identified patent and that said Letters Patent are hereby corrected as shown below:

Column 19, line 7, "4-Cyanophenoxy-(4'-methylphenyl)"
should be
--4-Cyanophenoxy-(4'-methylphenyl)methane-- line 8, "4-Formylphenoxy-(4'-fluorophenyl)"
should be
--4-Formylphenoxy-(4'-fluorophenyl)-methane --

Column 31, line 30, "Q" should read -- q --.

Signed and Sealed this

Fifteenth Day of February 1977

[SEAL]

Attest:

RUTH C. MASON
Attesting Officer

C. MARSHALL DANN
Commissioner of Patents and Trademarks